(12) United States Patent
Chan et al.

(10) Patent No.: US 6,890,913 B2
(45) Date of Patent: May 10, 2005

(54) CHITOSANS

(75) Inventors: Hing-Yuen Chan, Miaoli (TW);
Mei-Huei Chen, Hsinchu (TW);
Su-Hui Chuang, Hsinchu (TW);
Hsueh-O Chang, Hsinchu (TW);
Shu-Wan Wang, Taipei (TW);
Jian-Chyi Chen, Miaoli (TW);
Shiaw-Min Hwang, Hsinchu (TW);
Gwo-Fang Yuan, Hsinchu (TW)

(73) Assignee: Food Industry Research and Development Institute, Hsinchu (TW)

( * ) Notice: Subject to any disclaimer, the term of this patent is extended or adjusted under 35 U.S.C. 154(b) by 46 days.

(21) Appl. No.: 10/374,193

(22) Filed: Feb. 26, 2003

(65) Prior Publication Data

US 2004/0167323 A1 Aug. 26, 2004

(51) Int. Cl.[7] ...................... A61K 31/722; C08B 37/08; C12P 19/04
(52) U.S. Cl. ............................. 514/55; 514/54; 536/20; 536/18.7; 435/101; 435/911
(58) Field of Search ....................... 514/55, 54; 536/20, 536/18.7; 435/101, 911

(56) References Cited

U.S. PATENT DOCUMENTS

| 5,232,842 A | 8/1993 | Park et al. ................... 435/101 |
| 5,762,903 A | 6/1998 | Park et al. .................. 424/1.29 |
| 6,255,085 B1 * | 7/2001 | Chen et al. |

FOREIGN PATENT DOCUMENTS

| EP | 0 183 556 | 6/1986 | ........... A61K/31/73 |
| EP | 0 531 991 A2 | 3/1993 | ............ C12P/19/04 |
| EP | 0 730 870 A1 | 9/1996 | ........... A61K/51/06 |
| JP | 63-246332 | 10/1988 | ........... A61K/31/73 |
| JP | 6-22725 | 2/1994 | ............. A23L/1/30 |
| JP | 7-2679 | 1/1995 | ........... A61K/31/73 |
| JP | 9-48734 | 2/1997 | ........... A61K/36/78 |
| WO | WO 02/34287 | 5/2002 | ........... A61K/39/39 |

OTHER PUBLICATIONS

Muhannad et al. (European Journal of Pharmaceutics and Biopharmaceutics (Jan. 2002) 53 (1) 115–23) (abstract sent).*
Hagiwara et al. (JP 01061429 A2) (abstract sent).*
Caldwell, Cytotoxic Activity of Two Polyaspartamide–based Monoamineplatinum(II) Conjugates Against the HeLa Cancer Cell Line, Applied Organometallic Chemistry 13:189–194, 1999.
Chen et al., "Inhibitory Effect of Chitosan Derived From Fungus on Tumor Cells", JAACT/ESACT '98 Meeting, Jul. 26–30, 1998, Kyoto, Japan, P–58.
Database BIOSIS, Biosciences Information Service, Philadelphia, PA, US; PREV200200447604, 2002, XP002246933.
Database CAPLUS, Chemical Abstracts Service, Columbus, Ohio, US, retrieved from CAPLUS No. 2000:281857, XP002246881.
Eagle et al., "Cytotoxicity in Human Cell Cultures as a Primary Screen for the Detection of Anti–Tumor Agents", Cancer Research 18: 1017–1025, 1958.
Fichera et al., "2–6–Di(heteroarylvinyl)pyridines as New Potential Antitumor Agents", J. Phys. Org. Chem. 13:344–346, 2000.
Koide, "Chitin–Chitosan: Properties, Benefits and Risks", Nutrition Research 18:1091–1101, 1998.
Lu et al., "Resveratrol, a Natural Product Derived From Grape, Exhibits Antiestrogenic Activity and Inhibits the Growth of Human Breast Cancer Cells", J. of Cellular Physiology 179:297–304, 1999.
Monks et al., "Feasibility of a High–Flux Anticancer Drug Screen Using a Diverse Panel of Cultured Human Tumor Cell Lines", Articles 83:757–766, 1991.
Rexen et al., "Investigation of Different Modifications to the Tetrazolium Based Colorimetric Viability Assay", Biotechnology Techniques 6:255–260, 1992.
Rogozhin et al., "The Partial Acidic Hydrolysis of Chitosan", Polymer Science U.S.S.R. 30:607–614, 1988, XP000133818.
Sirica et al., "Selective Aggregation of L1210 Leukemia Cells by the Polycation Chitosan", J. of the National Cancer Institute, 47:377–388, 1971.
Shahidi et al., "Food Applications of Chitin and Chitosans", Trends in Food Science & Technology 10:37–51, 1991.
Suzuki et al., "Antitumor Effect of Hexa–N–Acetylchitohexaose and Chitohexaose", Carbohydrate Research 151:403–408, 1986.
Tan et al., "The Degree of Deacetylation of Chitosan: Advocating the First Derivative UV–Spectrophotometry Method of Determination", Talanta 45:713–719, 1998.
Torzsas et al., "The influence of High and Low Molecular Weight Chitosan on Colonic Cell Proliferation and Aberrant Crypt Foci Development in CF1 Mice", Fd Chem. Toxic. 34:73–77, 1996.
Tsukada et al., "Antimetastatic and Growth–inhibitory Effects of N–Acetylchitohexaose in Mice Bearing Lewis Lung Carcinoma", Jpn. J. Cancer Res. 81:259–265, 1990.

* cited by examiner

*Primary Examiner*—James O. Wilson
*Assistant Examiner*—Michael C. Henry
(74) *Attorney, Agent, or Firm*—Fish & Richardson P.C.

(57) ABSTRACT

A chitosan having a weight average molecular weight of 50,000–140,000 g/mole and a degree of deacetylation of 85–95%. Also disclosed are a method of preparing a chitosan from a fungus, and a method of using a chitosan for treating breast or cervical cancer.

18 Claims, No Drawings

CHITOSANS

BACKGROUND

Chitin is highly insoluble N-acetylated polymer of β-(1,4)-D-glucosamine. Chitosan is an acid-soluble deacetylated form of chitin. Chitin is commonly found in exoskeletons of marine invertebrates and cuticles of insects. Both chitin and chitosan are also present in the cell wall of most *Zygomycetes* as.

Chitosan can be obtained by deacetylating chitin prepared from crab or shrimp shell. However, this process fails to produce chitosan of uniform quality. Moreover, the composition of crab or shrimp shell is highly dependent upon seasonal and environmental factors. Therefore, it is difficult to obtain from crab or shrimp chitosan with consistent physio-chemical properties. Chitosan can also be obtained from a filamentous fungus of the family *Mucoraceae*. No chemical deacetylation is necessary in the process. As a result, the quality of fungal chitosan is more consistent.

SUMMARY

The present invention relates to a novel chitosan, production of chitosan from a fungus, and use of chitosan for treating cancer.

A chitosan of the invention has a weight average molecular weight of 50,000–140,000 g/mole and a degree of deacetylation of 85–95%.

Weight average molecular weight ($M_w$) is the first moment of a plot of the weight of polymer in each molecular weight range against molecular weight. It is calculated as follows:

$$M_w = \frac{\sum_i N_i M_i^2}{\sum_i N_i M_i}$$

The summations are over all polymer molecules (i=1 to i=∞) of different sizes and $N_i$ is the number of molecules (in moles) whose weight is $M_i$. The value of $M_w$ can be determined, e.g., by light scattering, sedimentation equilibrium measurements, or any other methods known in the art.

Deacetylation involves removal of acetyl groups from the molecular chain of chitin, leaving behind an amino group (—$NH_2$). The degree of deacetylation (DD), which represents the content of free amino groups in the polysaccharides, can be determined, e.g., by ninhydrin test, linear potentiometric titration, colloidal titration, near-infrared spectroscopy, nuclear magnetic resonance spectroscopy, hydrogen bromide titrimetry, infrared spectroscopy, UV-spectrophotometry, first derivative UV-spectrophotometry, enzymatic determination, or any other methods known in the art.

A chitosan of the invention can be prepared, e.g., from a fungus. Suitable fungi include fungi of the *Mucoraceae* family such as those in the *Actinomucor* genus. A particular example of the fungi useful for the present invention is *Actinomucor taiwanesis*. Chitosan can be obtained by growing a fungus culture at a temperature of 15–24° C. and isolating a chitosan from the culture.

Chitosan can be used in a pharmaceutical composition with a pharmaceutically acceptable carrier to treat cancer. In one aspect, the invention features a method of treating breast cancer. The method involves administering to a subject in need thereof an effective amount of a chitosan, e.g., a chitosan that has a weight average molecular weight of 50,000–140,000 g/mole and a degree of deacetylation of 85–95%. In another aspect, the invention features a method of treating cervical cancer by administering to a subject in need thereof an effective amount of a chitosan of the invention.

The present invention provides a novel chitosan with anti-cancer activities. The details of one or more embodiments of the invention are set forth in the accompanying description below. Other features, objects, and advantages of the invention will be apparent from the description, and from the claims.

DETAILED DESCRIPTION

This invention is based on the unexpected discovery that chitosan prepared from *Actinomucor taiwanensis* inhibits growth of human cervix epithelioid carcinoma cell (HeLa) and human breast carcinoma cell (MCF-7) in vitro.

Accordingly, the present invention features a method of preparing a chitosan from a fungus. The method involves growing a fungus culture at a temperature of 15–24° C. and isolating a chitosan from the culture.

Fungi useful for the present invention include those of the *Mucoraceae* family (e.g., the *Actinomucor* genus). These fungi can be obtained from various publicly available fungi collection resources. For instance, the fungus (*Actinomucor taiwanensis*) used in the examples described below is available upon request from the Bioresource Collection and Research Center (BCRC, Catalog No. BCRC31159), Food Industry and Research Development Institute, located at No. 331, Shih-Ping Road, Hsinchu 300, Taiwan, Republic of China.

Fungi can be cultivated in accordance with the procedures well known in the art. For example, YM agar can be inoculated with a fungus, and the inoculated agar incubated at 25–37° C. for 3 to 6 days. Spores obtained from the fungus are suspended in liquid to achieve a $10^4$ to $10^7$ cfu/ml stock. This stock is directly inoculated into a fermentation medium.

The fermentation medium has an initial pH ranging from 3 to 6 (e.g., between 3 and 5), and can contain 5 to 50 g/L (e.g., 20 g/L) of glucose, 5 to 60 g/L (e.g., 10 g/L) of peptone, 0.1 to 5 g/L (e.g., 1 g/L) of yeast extract, or other suitable ingredients. The medium can further contain 0.01 to 30 g/L of $(NH_4)_2SO_4$, 0 to 3 g of $K_2HPO_4$, 0 to 3 g of NaCl, 0 to 15 g of $MgSO_4 \cdot 7H_2O$ and 0 to 0.3 g/L $CaCl_2$. The fungus is grown in the fermentation medium at 15–24° C. for an additional 2 to 4 days.

Chitosan can be isolated and purified from fungal mycelia by alkaline and acid treatment as described in U.S. Pat. No. 6,255,085 B1. The cell mass is separated from the fermentation broth and washed with distilled water. The cells are then treated with 0.5 to 2 N NaOH, and the alkaline mixture incubated at 121° C. for 15 min. The solid material is then pelleted by centrifugation and washed with distilled water and ethanol. The washed material is treated with 2% acetic acid solution and incubated at 95° C. for 12 hours. The resulting slurry is then isolated by centrifugation, yielding an acid-soluble supernatant. The pH of the supernatant is adjusted to 10 with 2 N NaOH, thereby precipitating out the chitosan. The purified chitosan is finally washed with distilled water and freeze-dried.

Weight average molecular weight ($M_w$) and degree of deacetylation (DD) of chitosan can be measured, e.g., by the methods of $GPC/SEC^3$ and first derivative UV-spectrophotometry, respectively, or by any other methods known in the art. As described in the examples below, the $M_w$ and DD of the fungal chitosan prepared according to the just-mentioned method are 50,000–140,000 g/mole and 85–95%.

Unexpectedly, the fungal chitosan exhibits potent cytotoxic activity against the growth of HeLa and MCF-7 cells at a concentration of 10 ppm (about $10^{-7}$ M), whereas crustacean chitosan does not show this effect. Moreover, the fungal chitosan has no cytotoxicity against human embryonal lung cells (MRC-5) or other tumor cell lines such as human gastric carcinoma cell line (AGS) and human hepatoma cell line (Hep G2).

Accordingly, the present invention features a pharmaceutical composition that contains a pharmaceutically acceptable carrier and an effective amount of a chitosan that has a weight average molecular weight of 50,000–140,000 g/mole and a degree of deacetylation of 85–95%. The pharmaceutical composition can be used to prevent and treat breast or cervical cancer. The pharmaceutically acceptable carrier includes a solvent, a dispersion medium, a coating, an antibacterial and antifungal agent, and an isotonic and absorption delaying agent. An "effective amount" is the amount required to confer therapeutic effect. The interrelationship of dosages for animals and humans (based on milligrams per meter squared of body surface) is described by Freireich, et al. (1966) Cancer Chemother. Rep. 50:219. Body surface area can be approximately determined from height and weight of the subject. See, e.g., p537, Scientific Tables, Geigy Pharmaceuticals, Ardley, N.Y., 1970. Effective doses also vary, as recognized by those skilled in the art, dependent on route of administration, excipient usage, and the like.

A chitosan of the invention can be formulated into dosage forms for different administration routes utilizing conventional methods. For example, it can be formulated in a capsule, a gel seal, or a tablet for oral administration. Capsules can contain any standard pharmaceutically acceptable materials such as gelatin or cellulose. Tablets can be formulated in accordance with conventional procedures by compressing chitosan with a solid carrier and a lubricant. Examples of solid carriers include starch and sugar bentonite. A chitosan of the invention can also be administered in a form of a hard shell tablet or a capsule containing a binder, e.g., lactose or mannitol, a conventional filler, and a tableting agent. The pharmaceutical composition can be administered via the parenteral route. Examples of parenteral dosage forms include aqueous solutions, isotonic saline or 5% glucose of the active agent, or other well-known pharmaceutically acceptable excipient. Cyclodextrins, or other solubilizing agents well known to those familiar with the art, can be utilized as pharmaceutical excipients for delivery of the therapeutic agent.

The efficacy of a composition of this invention can be evaluated both in vitro and in vivo. See, e.g., the examples below. Briefly, the composition can be tested for its ability to inhibit the growth of breast or cervical caner cells in vitro. For in vivo studies, the composition can be injected into an animal and its cancer-inhibitory effects are then accessed. Based on the results, an appropriate dosage range and administration route can be determined.

Also within the scope of the invention is a method of preventing and treating breast cancer or cervical cancer by administering to a subject in need thereof an effective amount of a chitosan (e.g., the above-mentioned fungal chitosan). A subject to be treated can be a cancer patient or an individual who is at risk for developing breast or cervical cancer due to genetic or environmental factors. This method can be performed alone or in conjunction with other drugs or therapy.

Generally, a chitosan is suspended in a pharmaceutically-acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily. The dosage required depends on the choice of the route of administration; the nature of the formulation; the nature of the subject's illness; the subject's size, weight, surface area, age, and sex; other drugs being administered; and the judgment of the attending physician. Suitable dosages are in the range of 0.01–100.0 mg/kg. Wide variations in the needed dosage are to be expected in view of the variety of chitosans available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Preparation of Fungal Chitosans (1) Preparation of Fungal Chitosan A

Spore suspension of *Actinomucor taiwanensis* from 4-day slant cultures was inoculated directly into 1-L shake flasks containing 400 ml of fresh fermentation medium. Fermentation was carried out at a temperature of 22° C. for 50 hrs with shaking at 200 rev./min. Each liter of medium contained 10 g peptone, 20 g glucose, 1 g yeast extract, 5 g $(NH_4)_2SO_4$, 1 g $K_2HPO_4$, 1 g NaCl, 5 g $MgSO_4.7H_2O$, and 0.1 g $CaCl_2$. The initial pH was adjusted to 4.0.

Cell mass was recovered from the fermented broth and treated with 1 N sodium hydroxide solution at 121° C. for 15 min. The alkali-insoluble material was suspended in 2% acetic acid, and the mixture incubated at 95° C. for 12 hrs to solubilize the chitosan. The solubilized chitosan was precipitated by adjusting pH of the acid-soluble supernatant to 10. The precipitate (Fungal Chitosan A) was then washed and dried.

(2) Preparation of Fungal Chitosan B

Spore suspension of *Actinomucor taiwanensis* from 4-day slant cultures was inoculated directly into a 5-L fermentor containing 3 L of fresh fermentation medium. Fermentation was carried out at a temperature of 22° C., agitation of 400 rpm, and aeration of 3 L/min. for 50 hrs. Each liter of medium contained 10 g peptone, 20 g glucose, 1 g yeast extract, 5 g $(NH_4)_2SO_4$, 1 g $K_2HPO_4$, 1 g NaCl, 5 g $MgSO_4.7H_2O$, and 0.1 g $CaCl_2$. The initial pH was adjusted to 4.0.

Cell mass was separated from the fermented broth and the chitosan (Fungal Chitosan B) was prepared as described above in section (1).

Anti-tumor Activities of Fungal Chitosans

HeLa cell (BCRC60005) and MCF-7 cell (BCRC60436) were obtained from the Bioresource Collection and Research Center, Taiwan, R.O.C. Cell suspension was trypsinized with 0.05% trypsin/0.53 mM EDTA 4Na in Hank's Balanced Salt Solution (HBSS), disaggregated through pipetting, and counted with a hematocytometer. Cells were resuspended in MEM medium (with 10% serum) at $8.35\times10^3$ (for HeLa) or $1.67\times10^4$ (for MCF-7) cells per ml. Cell suspension (180 µl) was seeded in a 96-well tissue culture plate and was incubated at 37° C. in a 5% $CO_2$ atmosphere for 17–20 hrs.

Various chitosan solutions (in Dulbecco's phosphate-buffered saline (D-PBS) containing $5\times10^{-3}$ M acetic acid, 20 µl each) were added into the wells, and the cells were incubated at 37° C. in a 5% $CO_2$ atmosphere for 3 days. The final concentration of each chitosan was 10 ppm (about $10^{-7}$ M).

The viability of the cells was analyzed using the MTT (3-(4,5-dimethyl-thiazol-2-yl) 2,5-diphenyl tetrazolium bromide) method. 20 µl of 5 mg/ml of MTT solution in D-PBS was added to each well, and the cells were incubated at 37° C. in a 5% $CO_2$ atmosphere for 4 hrs. The medium was then removed. 100 µl of DMSO was added into each well, and the plate was shaked for 5 min. The optical density of each well was then measured at both a testing wavelength (540 nm) and a reference wavelength (690 nm).

Chitosans used in this study included Fungal Chitosan A, Fungal Chitosan B, Crab Shell Chitosan I, Crab Shell Chitosan II, Crab Shell Chitosan III, and Crab Shell Chitosan IV.

Degree of deacetylation of each chitosan was determined by first derivative UV-spectrophotometry as described in Tan et al. (1998) Talanta 45:713–719.

Molecular characteristics of each chitosan were determined using triple-detection GPC/SEC[3]. Chitosan samples were prepared at 2.5 mg/ml in a mobile phase and were heated at 90° C. for 3 hr. The mobile phase was 0.35 N acetic acid, 8.2 g/L sodium acetate, pH4.1; and the flow-rate was 0.7 ml/min. Sample injection volume was 100 µl, and SEC[3] separation was performed on TSK GPC column $GMPW_{XL}$ from Tosoh, Japan. Detectors used for triple-detection analysis were refractive index detector (Waters Co.), differential viscometer detector (Viscotek model T60), and light scattering detector (Viscotek model T60). Data was collected and processed with TriSEC software using the three detectors simultaneously.

The weight average molecular weight ($M_w$), number average molecular weight ($M_n$), polydispersity index ($M_w/M_n$), radius of gyration (Rgw), weight average intrinsic viscosity ($[\eta]_w$), and degree of deacetylation (DD) of each chitosan are listed in Table 1 below.

TABLE 1

Molecular characteristics and degree of deacetylation of chitosans used for anti-tumor activity assay

| Chitosans | $M_w \times 10^{-3}$ (g/mol) | $M_n \times 10^{-3}$ (g/mol) | $M_w/M_n$ | Rgw (nm) | $[\eta]_w$ (ml/g) | DD (%) |
|---|---|---|---|---|---|---|
| Fungal Chitosan A | 116.5 | 58.0 | 2.01 | 18.0 | 1.70 | 90.1 |
| Fungal Chitosan B | 94.4 | 89.4 | 1.06 | 11.0 | 0.44 | 87.0 |
| Crab Shell Chitosan I | 317.2 | 286.3 | 1.12 | 41.1 | 6.40 | 79.7 |
| Crab Shell Chitosan II | 163.5 | 115.3 | 1.42 | 28.9 | 4.66 | 83.5 |
| Crab Shell Chitosan III | 140.7 | 80.5 | 1.75 | 24.7 | 3.56 | 78.1 |
| Crab Shell Chitosan IV | 88.5 | 48.6 | 1.83 | 17.1 | 1.90 | 78.5 |

Unexpectedly, both HeLa cells and MCF-7 cells were found to be sensitive to fungal chitosans (A and B) but not to crab shell chitosans (I–IV). The fungal chitosans (A and B) selectively inhibited tumor growth with inhibition ratios of over 30% (see Table 2 below). On the other hand, the fungal chitosans (A and B) did not significantly inhibit the growth of human embryonal lung cells (MRC-5) or other carcinoma cell lines such as human gastric carcinoma cell line (AGS) and human hepatoma cell line (Hep G2).

TABLE 2

Effects of various chitosans on growth of HeLa cells and MCF-7 cells

| Samples | n = | Cell growth percentage (mean ± S.D.)[a,b] | |
|---|---|---|---|
| | | HeLa cells | MCF-7 cells |
| Control (no chitosan) | 6 | 100 ± 4 | 100 ± 5 |
| Fungal Chitosan A | 6 | 65 ± 3 | 57 ± 6 |
| Fungal Chitosan B | 6 | 69 ± 2 | 69 ± 4 |
| Crab Shell Chitosan I | 4 | 98 ± 11 | 96 ± 3 |
| Crab Shell Chitosan II | 4 | 95 ± 7 | 98 ± 7 |
| Crab Shell Chitosan III | 4 | 94 ± 9 | 92 ± 6 |
| Crab Shell Chitosan IV | 4 | 99 ± 5 | 98 ± 3 |

[a]Each value represents the average cell growth percentage (%) of 4 or 6 replicates and the standard deviation.
[b]Cell growth percentage = (number of chitosan-treatmented cells/number of control cells) × 100%.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A chitosan having a weight average molecular weight of 50,000–140,000 g/mole and a degree of deacetylation of 85–95%, wherein the chitosan is prepared from a fungus.

2. A pharmaceutical composition comprising a chitosan of claim 1 and a pharmaceutically acceptable carrier.

3. A method of treating breast cancer, the method comprising administering to a subject in need thereof an effective amount of chitosan of claim 1 prepared from a fungus.

4. The method of claim 3, wherein the chitosan is prepared from a fungus of the *Mucoraceae* family.

5. The method of claim 4, wherein the chitosan is prepared from a fungus of the *Actinomucor* genus.

6. The method of claim 5, wherein the chitosan is prepared from *Actinomucor taiwanesis*.

7. A method of treating cervical cancer, the method comprising administering to a subject in need thereof an effective amount of a chitosan that has a weight average molecular weight of 50,000–140,000 g/mole and a degree of deacetylation of 85–95%, wherein the chitosan is prepared from a fungus.

8. The method of claim 7, wherein the chitosan is prepared from a fungus of the *Mucoraceae* family.

9. The method of claim 8, wherein the chitosan is prepared from a fungus of the *Actinomucor* genus.

10. The method of claim 9, wherein the chitosan is prepared from *Actinomucor taiwanesis*.

11. A method of preparing a chitosan from a fungus, the method comprising:

growing a fungus culture at a temperature of 15–24° C., and isolating a chitosan from the culture, wherein the chitosan has a weight average molecular weight of 50,000–140,000 g/mole and a degree of deacetylation of 85–95%.

12. The method of claim 11, wherein the fungus is a fungus of the *Mucoraceae* family.

13. The method of claim 12, wherein the fungus is a fungus of the *Actinomucor* genus.

14. The method of claim 13, wherein the fungus is *Actinomucor taiwanesis*.

15. A chitosan prepared by the method of claim 11, wherein the chitosan has a weight average molecular weight of 50,000–140,000 g/mole and a degree of deacetylation of 85–95%.

16. The chitosan of claim 15, wherein the fungus is a fungus of the *Mucoraceae* family.

17. The chitosan of claim 16, wherein the fungus is a fungus of the *Actinomucor* genus.

18. The chitosan of claim 17, wherein the fungus is *Actinomucor taiwanesis*.

* * * * *